(12) United States Patent
Fleischer et al.

(10) Patent No.: US 8,033,159 B2
(45) Date of Patent: Oct. 11, 2011

(54) SENSOR AND OPERATING METHOD FOR DETECTING SOOT

(75) Inventors: Maximilian Fleischer, Höhenkirchen (DE); Roland Pohle, Herdweg (DE); Kerstin Wiesner, Putzbrunn (DE)

(73) Assignee: Siemens VDO Automotive AG, Regensburg (DE)

( * ) Notice: Subject to any disclaimer, the term of this patent is extended or adjusted under 35 U.S.C. 154(b) by 451 days.

(21) Appl. No.: 11/988,125

(22) PCT Filed: Jun. 27, 2006

(86) PCT No.: PCT/EP2006/063570
§ 371 (c)(1), (2), (4) Date: Dec. 28, 2007

(87) PCT Pub. No.: WO2007/000446
PCT Pub. Date: Jan. 4, 2007

(65) Prior Publication Data
US 2009/0126458 A1    May 21, 2009

(30) Foreign Application Priority Data
Jun. 28, 2005  (DE) .................. 10 2005 030 134

(51) Int. Cl.
*G01N 37/00* (2006.01)
(52) U.S. Cl. ...................................... 73/28.01
(58) Field of Classification Search .................. 73/28.01
See application file for complete search history.

(56) References Cited

U.S. PATENT DOCUMENTS

| | | | |
|---|---|---|---|
| 3,196,499 A | 7/1965 | Houvener | |
| 4,300,990 A * | 11/1981 | Maurer | 204/412 |
| 4,307,061 A | 12/1981 | Sarholz | |
| 4,656,832 A | 4/1987 | Yukihisa et al. | |
| 5,008,628 A * | 4/1991 | Krigmont et al. | 324/693 |
| 6,483,079 B2 * | 11/2002 | Sato et al. | 219/270 |
| 6,634,210 B1 * | 10/2003 | Bosch et al. | 73/23.33 |
| 7,541,004 B2 * | 6/2009 | Niksa et al. | 422/82.02 |
| 7,574,895 B2 | 8/2009 | Schnell et al. | |

(Continued)

FOREIGN PATENT DOCUMENTS

DE    3935149    2/1991

(Continued)

OTHER PUBLICATIONS

Horn P. et al. "Measurement of the degree of contamination in combustion gases of oil heatings", Technisches Messen TM, R. Oldenbourg publishing house, Munich, DE, Apr. 4, 1985, Band 52, No. 4, pp. 154-159, ISSN: 0171-8096, XP002135508.

(Continued)

*Primary Examiner* — Hezron E Williams
*Assistant Examiner* — Rodney T Frank
(74) *Attorney, Agent, or Firm* — Cozen O'Connor

(57) ABSTRACT

The invention relates to a sensor and a method for detecting soot, said method comprising the following steps: a first operating temperature is set on the sensor for a measuring phase, such that soot can be deposited on the surface of the substrate, but depositions interfering with the measurement of the soot are prevented; the time between the beginning of the measurement and the increase in conductivity between the electrodes is recorded; and a second operating temperature is set on the sensor for a regeneration phase, such that the deposited soot is burned with the oxygen in the test gas. The inventive product is a soot sensor for using in the automobile industry.

12 Claims, 4 Drawing Sheets

U.S. PATENT DOCUMENTS

| | | | |
|---|---|---|---|
| 2001/0013220 A1 | 8/2001 | Schonauer | |
| 2001/0051108 A1 | 12/2001 | Schoenauer | |
| 2003/0196499 A1* | 10/2003 | Bosch et al. | 73/865.5 |
| 2005/0279084 A1* | 12/2005 | Schmidt et al. | 60/295 |
| 2007/0119233 A1 | 5/2007 | Schnell et al. | |

FOREIGN PATENT DOCUMENTS

| | | |
|---|---|---|
| DE | 199 59 871 | 6/2001 |
| DE | 102 44 702 | 5/2003 |
| DE | 103 53 860 A1 | 6/2005 |
| JP | 59-197847 A | 11/1984 |
| JP | 05-501299 T | 3/1993 |
| WO | WO 2005/015192 A1 | 2/2005 |
| WO | WO 2005/050174 A1 | 6/2005 |
| WO | WO 2005/121761 A1 | 12/2005 |

OTHER PUBLICATIONS

German Office Action dated Apr. 19, 2007 from corresponding German Application.

German Office Action dated Jul. 25, 2006 from corresponding German Application.

Search Report dated Jun. 28, 2005 for the underlying International PCT Application No. PCT/EP2006/063570.

* cited by examiner

FIG 1
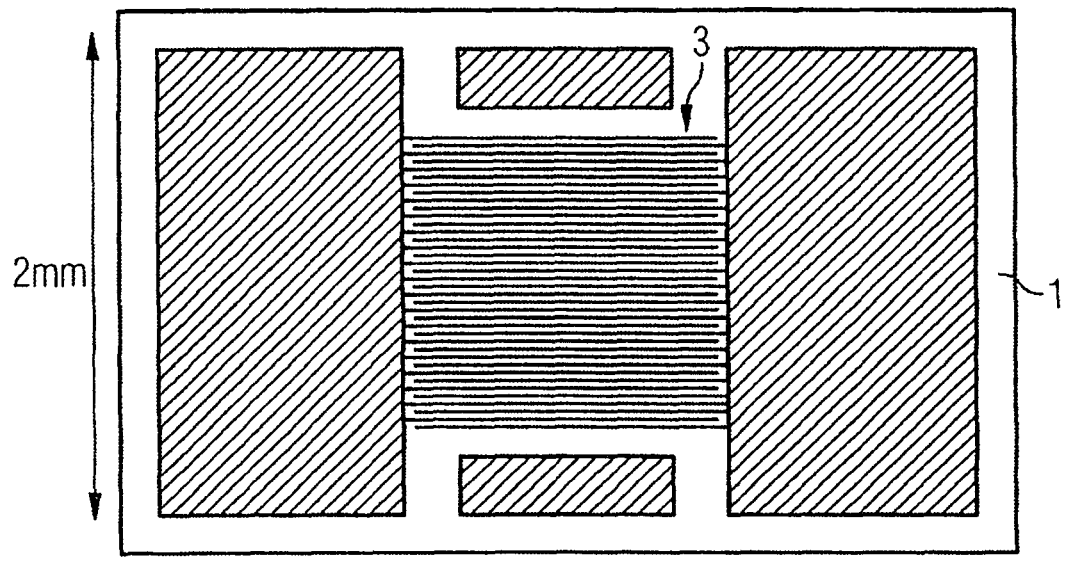
2mm
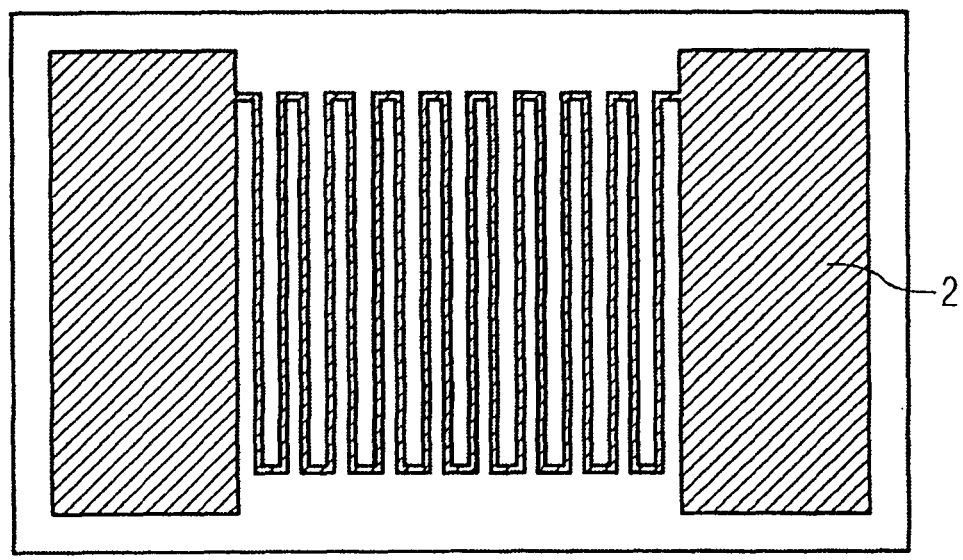

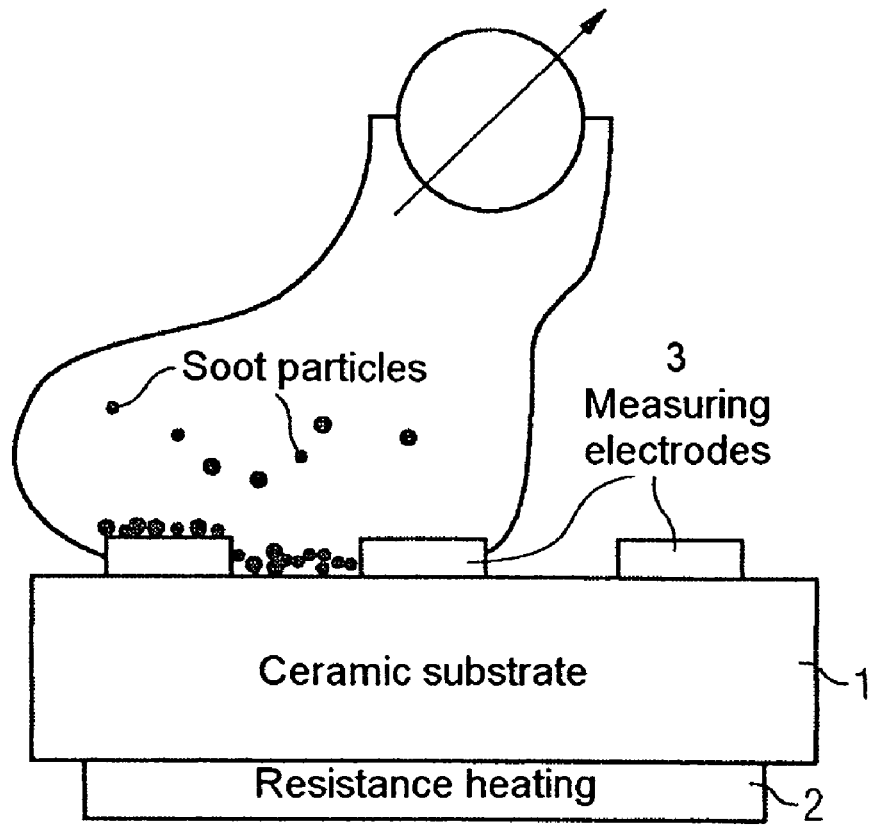
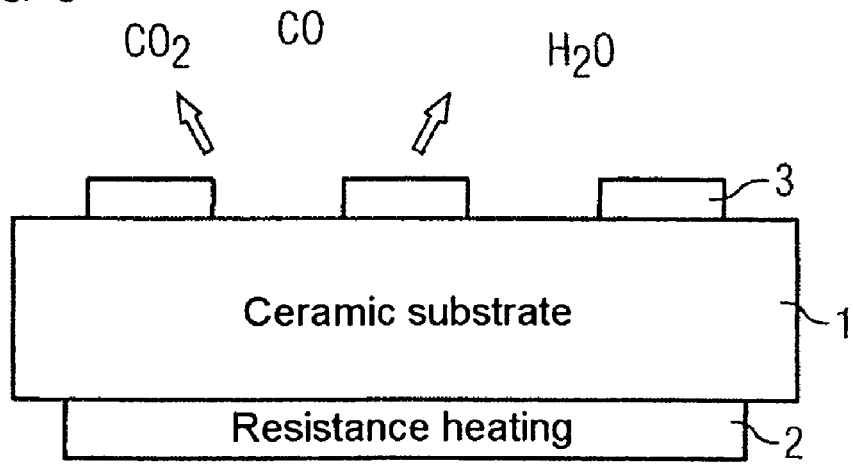

SENSOR AND OPERATING METHOD FOR DETECTING SOOT

CROSS REFERENCE TO THE RELATED APPLICATIONS

This is a U.S. national stage of application No. PCT/EP2006/063570, filed on 27 Jun. 2006. Priority is claimed on the following application: DE 10 2005 030 134.7, filed Jun. 28, 2005, the content of which is incorporated herein by reference.

BACKGROUND OF THE INVENTION

The invention relates to a sensor and an operating method of the sensor for the detection of soot in a measurement gas volume. Both the establishment of whether soot is present in the measurement gas and the concentration thereof are considered.

The accumulation of carbon dioxide in the atmosphere is being discussed from a variety of standpoints nowadays. This is associated with the fact that the availability of fossil fuels is limited. As a reaction to this, by way of example, combustion processes are being optimized thermodynamically, such that their efficiency is improved. In the motor vehicle sector, this is manifested in the increasing use of diesel vehicles. The disadvantage of this combustion technology however, in comparison with optimized spark ignition engines, is a significantly increased emission of soot. In addition, the formation thereof virtually cannot be prevented by combustion-technological measures. Soot is highly carcinogenic particularly due to the deposition of polycyclic aromatic compounds (PAH), and various regulations have already reacted to this. Thus, for example European exhaust gas emission standards are associated with maximum limits for soot emission. Therefore, there is the need to specify an inexpensive sensor technology that measures the soot content in exhaust gases.

The use of such soot sensors can be used both for the measurement of the soot currently being emitted, in order that the engine management in an automobile acquires information in a current driving situation in order to reduce emissions by means of technical control adaptations, and for performing active exhaust gas purification by means of so-called exhaust gas soot filters. In the latter case, use is made of regenerable filters which filter out a substantial part of the soot content from the exhaust gas. Soot sensors are required for the detection of soot in order to monitor the function of the soot filters, or in order to control the regeneration cycles thereof.

There have been various approaches for detecting soot in the prior art. An approach that has been pursued to a great extent in laboratories consists in using the light scattering by the soot particles. This procedure is suitable for complex measuring instruments. Where an attempt is made to use this also as a mobile sensor system in exhaust gas, it must be established that such approaches for realizing a cost-effective sensor in a motor vehicle are associated with high costs owing to the complex optical construction. Furthermore, there are unresolved problems with regard to the contamination of the required optical windows by combustion exhaust gases.

The published German patent application DE 199 59 871 A1 describes a sensor and operating method, both of which are based on thermal considerations. The sensor comprises an openly porous shaped body such as, for example, a honeycomb-shaped ceramic, a heating element and a temperature sensor. If the sensor is brought into contact with a measurement gas volume, then soot deposits on it. For measurement purposes, the soot deposited over a period of time is ignited with the aid of the heating element and burned. The temperature increase that arises during combustion is measured. Although this is a practicable procedure in constant environmental conditions, under the conditions of a motor vehicle exhaust section with greatly fluctuating flows and exhaust gas temperatures the measurement of the relatively small temperature increase proves to be an extremely difficult problem.

In principle, it is possible to use two methods for measuring soot. One is based on an electric field between two electrodes at which the measurement gas volume loaded with soot is present, the soot causing an ionization current. One embodiment of this principle is known from the published German patent application DE 102 44 702 A. In this case, the exhaust gas flow passes two electrodes which are provided with an electrical insulation layer and between which is situated the soot-containing gas to be examined.

The electrodes are operated with an AC voltage of between 1 and 10 kV. Between the electrodes, depending on the soot concentration in the measurement gas, a dielectrically impeded discharge is performed and the currents that occur are measured. For motor vehicle operation, this method is not practicable insofar as its realization requires high voltages and complicated measurement technology. Secondly, the changing gaseous exhaust gas constituents will entail a significant measurement corruption as a result of interfering gas influencing the ionization current.

SUMMARY OF THE INVENTION

It is therefore an object of the invention to provide a sensor and operating methods by which it is possible to detect soot, wherein the detection can be recorded rapidly and reproducibly.

These and other objects and advantages are achieved by using a sensor that measures the dielectric surface conductivity, by means of two electrodes, for example, such that it is possible to detect a quantity of soot that has deposited on the surface. By virtue of a planar embodiment of the sensor, even small changes in conductivity can be identified, for example, if a film of soot forms on the surface.

In this case, it is particularly advantageous if finely divided, electrically conductive particles that are not in contact with one another are introduced between the measuring electrodes, which has the effect that a measurable conductivity occurs even in the case of a considerably reduced quantity of soot or film thickness.

Advantages with regard to the generation of a measurement signal are afforded by an interdigital structure of the measuring electrodes. Such a structure is embodied for instance like two intermeshed comblike structures.

If a resistance sensor according to the invention is embodied doubly or multiply, then it can be ensured that, owing to required regeneration phases, there is nevertheless one sensor in a measuring phase at any time.

In order to protect the sensor, in particular the measuring electrodes or else the temperature sensor or the heating system, thin coatings are applied, which are finely porous, for example, in order—despite the protective effect—to permit a measurement gas flow, or the coatings are formed such that they themselves have a sufficient electrical conductivity, such that no impermissible corruption of the sensor signal is produced by the electrical resistance produced by the coating.

For the construction of the sensor with regard to reliable signal generation, it is highly advantageous to apply an electrically highly insulating layer to a generally likewise insulating substrate. The highly insulating layer can at the same time be embodied such that it is stable in the presence of exhaust gas.

It is possible to position an oxidation catalyst on the substrate surface or on the layer applied thereon. Here, the catalyst will generally be layered in the form of a dispersion, i.e., applied in a non-continuous form.

In order to save components on the sensor, the resistance heating system can simultaneously be operated as a temperature sensor. The heating system, preferably by itself or together with a temperature sensor, is coated with a protective layer or mounted in a multilayer construction in the interior of the sensor body.

As a basis for the use of a zero resistance as a starting point for resistance measurements, it is advantageous to design the substrate surface such that it has a defined basic conductance. In conjunction with the zero resistance, it is possible to determine the electrical functionality of the sensor in a self-monitoring unit or interrogation.

A soot sensor described is heated, such that in a measuring phase the operating conditions are set in such a way that constituents which can cause interference signals are not deposited in addition to the soot on the surface. When measurement has been concluded, a regeneration phase commences at elevated temperature. Depending on the application, a variant operated with at least two different temperatures can be used, such that the sensor measures and regenerates separately, or the sensor is kept at a temperature at which there is a dynamic equilibrium between measurement and regeneration. This means that the temperature level in conjunction with a defined catalytic activity of the surface permits a continuous combustion of the soot by oxygen present in the exhaust gas to proceed, with simultaneous measurement of the resistance for the soot covering, which is established dynamically. An increased electrical conductivity will be measured between the electrodes in accordance with the soot covering. The representation of the measurement signal can be based directly on the conductivity or can be determined by means of the temperature measurement, the conductivity then being regulated to a constant value. Using a substrate surface that provides a zero resistance, a self-monitoring of the sensor can advantageously be set up.

BRIEF DESCRIPTION OF THE DRAWINGS

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

FIG. 1 shows a top and bottom plan view illustrating the configuration for a particulate filter according to the invention;

FIGS. 2 and 3 schematically show in each case a cross section through a particulate filter according to the invention, the electrical evaluation being indicated;

DETAILED DESCRIPTION OF THE PREFERRED EMBODIMENTS

Figure 4:
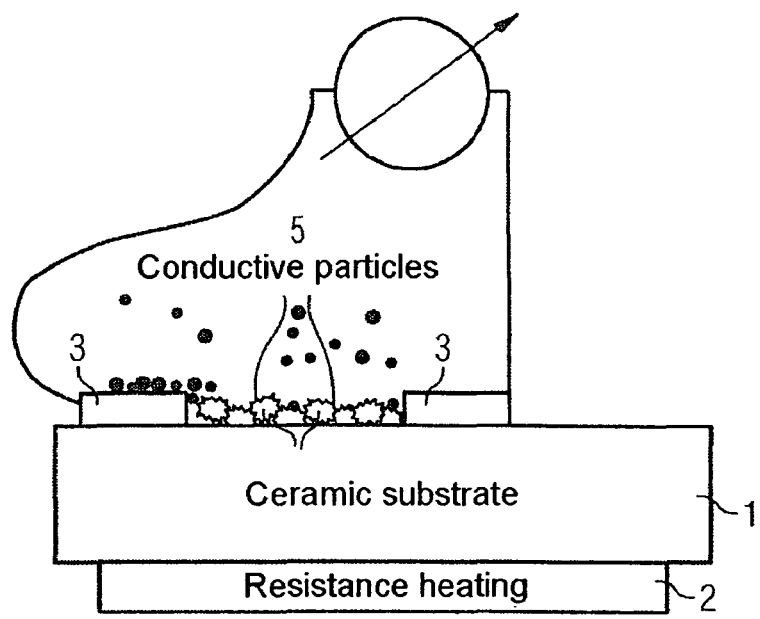
FIG. 4 shows an embodiment of the invention for improving the response behavior by means of finely divided conductive particles on the sensor surface.

The top half of FIG. 1 illustrates an interdigitally embodied and, hence, comblike structure of electrodes 3 between two large-area connection pads. On the substrate 1, which is generally a ceramic substrate, this measuring structure is situated on one side and the meandering structure of a heating system 2 is situated on the opposite side, said meandering structure being illustrated in the bottom half of FIG. 1.

A soot sensor can comprise a ceramic basic body, to which a soot-containing gas is applied at least on its surface, wherein a surface having predetermined electrically insulating or electrically weakly conductive properties has a catalytic effect with regard to the deposited soot. A temperature measurement of a temperature sensor is provided at the sensor. If soot from the soot-containing exhaust gas deposits on the surface, the electrical conductivity brought about by the deposited soot is measured between the electrodes and the presence of soot or a soot film is thus detected.

In a first embodiment of the inventive method, the sensor is maintained at a constant first temperature which lies, for example, within the range of 250-450° C. This prevents undesirable other exhaust gas constituents such as moisture, nitrogen oxides or sulfur dioxide, which can also cause an electrical conductivity on the surface, from depositing on said surface. The deposition of soot particles will take place, of course, wherein the measuring phase of the sensor begins at a specific temporal zero point and ends when a predetermined conductance has been reached by then between the electrodes. This is based on the fact that as time increases, an increasing deposition of soot particles on the surface of the sensor generates an electrical conductivity on the surface of the sensor, which is measurable. In this first phase of collecting soot particles, the time that elapses until the increased conductivity occurs is measured and serves as a measure of an average loading of the measurement gas with soot. When a specific conductivity is exceeded between the electrodes, the sensor element is heated to a defined second temperature, which typically lies between 500 and 800° C. At this temperature level, the soot particles are burned with the oxygen present in the exhaust gas, whereby the regeneration phase is represented. After the regeneration phase, the next measuring phase begins. Typical values for the time intervals for the measuring phase are for example, 30 seconds-300 seconds and for the regeneration phase are, for example, 10 seconds-40 seconds. The quantities are dependent on the type and duration of the exposure to soot.

In an advantageous embodiment of the method, at least two sensor elements are provided, wherein there is always at least one sensor element in the measuring phase and a continuous, i.e. interruption-free, measurement is thus ensured. In a second embodiment, the sensor is operated at a constant temperature lying within the range of 350 to 500° C. This higher temperature level, on the one hand, prevents the deposition of moisture, nitrogen oxides and sulfur dioxide, which could result in the generation of interference signals. The deposition of soot particles can take place, however. By virtue of the increased temperature in relation to the first temperature during the above-described first embodiment of the method, in conjunction with a predetermined catalytic activity of the surface, a continuous combustion of the soot by oxygen present in the exhaust gas will now also be present during the measuring phase, such that a covering of soot corresponding to the soot loading of the gas is established dynamically on the surface. An increased conductivity is measured between the two electrodes in accordance with the soot covering the surface. Temperature and catalytic activity are crucial for the soot covering in dynamic equilibrium between the soot deposition and catalytic combustion. The output signal of the sensor is then either represented by the respective increased conductivity or the temperature of the sensor element is regulated in such a way that a constant increased conductivity is achieved, the required temperature then representing the measurement signal.

The sensor generally comprises a ceramic basic body, for example, composed of aluminum oxide having a conductivity that is not specified in any greater detail. On the surface exposed to the measurement gas, it is preferably coated with an electrically highly insulating layer. The measuring electrodes are fitted on said layer. As a result, a very good electrical insulation of the electrodes is achieved and it is possible to detect even small electrical conductivities as a result of soot coverings. Materials provided for the insulation layer include a ceramic layer that effects very good electrical insulation, for example high-purity $Al_2O_3$, or AlN, having typical layer thicknesses of 10-100 μm. A highly insulating layer composed of $SiO_2$ or $Si_3N_4$ can also be applied by means of a method such as sputtering or CVD.

To protect the sensor or partial regions thereof, it is possible to apply a layer that is stable in respect of exhaust gas. It is also possible to provide a surface of the sensor which has a defined basic conductivity. In this case, a defined zero resistance is measured for the sensor element without any soot deposits. This is advantageous metrologically since an undefined high resistance is difficult to detect during sensor operation. This is applied to an extension of the operating method, in which, without soot deposition, the presence of the zero resistance indicates the electrical functionality of the sensor. As a result, self-monitoring is permitted. Suitable materials for a semiconducting layer that is stable in respect of exhaust gas are for example metal oxides such as $Ga_2O_3$, $CeO_2$ or $HfO_2$.

To support the regeneration in accordance with the first embodiment of the method, or to support the catalytic burning off of the soot in accordance with the second embodiment of the method, the surface of the sensor is assigned in a targeted manner a catalytic activity for the oxidation of soot deposited on the surface to form volatile gas components. This is achieved by applying an oxidation catalyst to the surface of the layer in the form of a dispersion. The dispersion supplies non-continuous regions such that the generally conductive catalyst materials cannot cause undesirable conductivities between the electrodes, which would corrupt the measurement signal. Materials for catalysts of this type are for example platinum metals such as Pt, Rh, Pa or the alloys thereof. It is also possible to use catalytically active oxides of secondary group metals such as, for example, $Fe_2O_3$, $CeO_2$, $MnO_2$, $Cr_2O_3$ or $HfO_2$.

By applying finely divided electrical particles that are not in contact with one another between the measuring electrodes, it is possible to considerably reduce the quantity of soot required for achieving a measurable conductivity.

The heating element comprises a metallic conductor track, e.g. composed of platinum or platinum metals or the alloys thereof. In this case, the heating resistance is a function of the temperature of the sensor element and the temperature can be determined by evaluating the present resistance of the heating element. Hence, the heating element acts as a temperature sensor. Precise knowledge of the temperature is necessary for the functioning of the sensor. In order to protect the heating system and/or the temperature sensor against ageing as a result of environmental influences, the environment is prevented from making contact therewith to the greatest possible extent. This is achieved either by applying a covering layer, for example, composed of materials having a high melting point such as glass, aluminum oxide, silicon dioxide or a combination thereof, or the components are fitted in the interior of a carrier, such as, for example, on the basis of embedding these elements in a multilayer construction.

The measuring electrodes 3 comprise, for example, metals that are stable in the presence of exhaust gas, such as Pt, Rh, alloys of platinum metals, chromium and nickel alloys, or else electrically conductive compounds that are stable in respect of exhaust gas, such as e.g. titanium nitrite/TiN, boron nitrite/BN, silicon carbide/SiC, boron carbite/$B_4C$ or tungsten silicide/$WSi_2$, or else platinum silicide/PtSi. The measuring electrodes may be provided with thin coatings in order to increase the stability in the exhaust gas. Here, the coating is so thin or else finely porous such that it does not cause any interfering electrical insulation. The chemical attack of the electrode material by corrosive exhaust gas constituents is reduced, however. Suitable materials for the layers are, for example, metals which are stable in the presence of exhaust gas but are semiconducting at elevated temperatures, such as gallium oxide or cerium oxide, or very thin layers composed of silicon oxide or aluminum dioxide.

Advantages of the invention include in particular providing a compact, simple and hence cost-effective construction with corresponding operating methods for determining the soot content in exhaust gases. The construction is formed from materials which impart to it the required durability and endurance strength with regard to aggressive and corrosive environmental conditions, such as an exhaust gas environment. The sensor is suitable for continuous monitoring of the exhaust gases and requires no maintenance or consumable replacement parts whatsoever. By virtue of the dosimeter method in accordance with the first embodiment of the cyclic method, the measurement principle refers directly to the specifications of the exhaust gas standard EURO 5. The soot emission per 100 km traveled is defined therein.

A schematic cross section of a disclosed sensor in accordance with the contemplated embodiments is illustrated in conjunction with FIG. 1, which also applies to FIGS. 2 and 3. The measuring electrodes 3 are illustrated on the top side of the sensor. In the measuring phase, the soot particles present in the gas phase deposit on the surface and lead to a measurable conductivity between the electrodes after the formation of a continuous current path. In the regeneration phase, the deposited soot particles are oxidized to form volatile gas components such as carbon dioxide or moisture (see, e.g., FIG. 3). FIG. 2 shows an illustration in which the sensor is in a measuring phase. In accordance with FIG. 3, the sensor is in the regeneration phase.

In the above described embodiment, the deposition of a certain number of soot particles that are in contact with one another is necessary in order to obtain a measurable signal. This number can be significantly reduced by applying, between the measuring electrodes with which contact is made externally, finely divided, conductive particles which reduce the total length of the path to be bridged by the soot particles to a fraction, as is illustrated in FIG. 4. It is thus possible both to considerably reduce the mass covering required for the response of the sensor and to increase the sensitivity to small particles. Particular attention is given to the small particles on account of their considerable health jeopardizing potential. In addition, when choosing a suitable sensor material for said conductive particles, e.g. platinum, it is possible to increase the catalytic activity of the surface and thus, to increase the effectiveness of the regeneration process. As a result, it becomes possible to reduce the regeneration duration and/or regeneration temperature.

Figure 5:
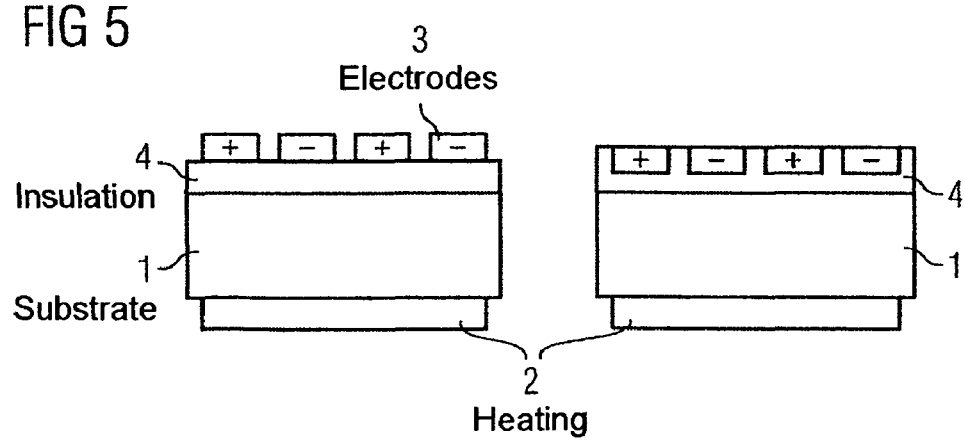
FIG. 5 shows two arrangements for increasing the sensitivity by improving the electrical insulation by means of an insulation layer deposited on the substrate.

In another embodiment, the insulation capability is increased by applying an additional insulating layer, as illustrated in FIG. 5. Here, the measuring electrodes 3 either bear on the insulating layer or are introduced into the insulating layer, thus giving rise to a plane surface structure for the best possible measurement of a thin film of soot. Consequently, it is also possible, in accordance with the contemplated embodiment shown in the right-hand half of FIG. 5, to prevent interruptions in the conductivity by the soot at vertical edges of the electrodes.

Figure 6:
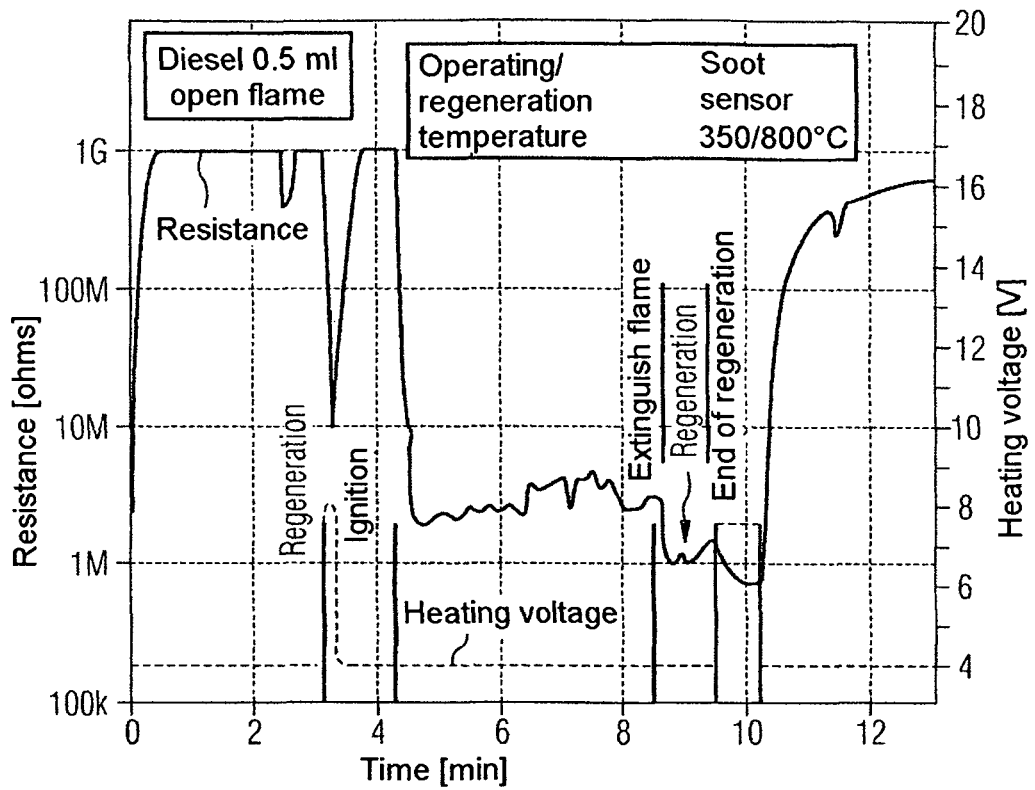
FIG. 6 shows a diagram showing conductivity measurements on a soot sensor according to the invention.

A measurement using a sensor constructed in accordance with FIG. 1 is illustrated in FIG. 6. In the course of the first minute of the measurement, the resistance of the sensor rises since desorption occurs during the heating phase to 350° C. After approximately 3 minutes, a regeneration step is performed at 800° C. Here, the resistance is reduced by virtue of an intrinsic conductivity of the substrate. After the sensor has again reached its operating temperature of 350° C., after approximately 4.3 minutes the sensor is exposed to the soot of an open diesel flame. After a few seconds after ignition, the sensor resistance falls steeply over a number of decades, and it reaches a stable value while soot is still being formed. As a result of the regeneration at 800° C. over approximately 9.5 minutes, the soot situated on the active sensor area is burned to form volatile gaseous components, primarily carbon dioxide, such that the resistance reassumes its original value.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. Moreover, it should be recognized that structures shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A sensor for detecting soot, comprising:
   a ceramic substrate having an electrically nonconductive surface exposed to a measurement gas;
   an electrode structure formed on a the surface of the ceramic substrate and having electrodes for measuring electrical conductivity of the sensor;
   finely divided, electrically conductive particles applied on the substrate surface between the electrodes to reduce the quantity of soot required for generating a measurable conductivity, the particles being spaced apart from each other;
   a heating system fitted to the substrate surface, said heating system setting a predefined operating temperature; and
   at least one temperature measuring device;
   wherein soot deposits present are detectable by measuring the conductivity between the electrodes.

2. The sensor as claimed in claim 1, wherein the predefined operating temperature is within a range of between approximately 250° C. to 450° C.

3. The sensor as claimed in claim 1, wherein the substrate surface has catalytic properties facilitating combustion of the soot.

4. The sensor as claimed in claim 1, wherein the substrate surface has catalytic properties facilitating combustion of the soot.

5. The sensor as claimed in claim 1, wherein in the electrodes are arranged in an interdigital manner.

6. The sensor as claimed in claim 1, and a further sensor identical to the sensor of claim 1 for simultaneous use.

7. The sensor as claimed in claim 1, further comprising a thin and finely porous coating covering the electrodes and increasing stability of the electrodes.

8. The sensor as claimed in claim 1, wherein at least one of the heating system and the at least one temperature sensor, in the case of surface mounting, is one of coated with a protective layer and mounted in a multilayer construction in an interior of a body of the sensor.

9. The sensor as claimed in claim 1, wherein one of the surface of the ceramic substrate and a layer applied to the surface of the ceramic substrate has a predetermined basic conductivity such that a zero resistance is defined.

10. The sensor as claimed in claim 1, wherein the soot deposits present are detectable by measuring the conductivity between the electrodes at the predefined operating temperature.

11. A sensor for detecting soot, comprising:
   a ceramic substrate having an electrically nonconductive surface exposed to a measurement gas;
   an electrode structure formed on a the surface of the ceramic substrate and having electrodes for measuring electrical conductivity of the sensor:
   a heating system fitted to the substrate surface, said heating system setting a predefined operating temperature;
   at least one temperature measuring device; and
   an oxidation catalyst comprising a dispersion applied on the one of the ceramic substrate and the electrical insulating layer provided on the ceramic substrate such that a continuous layer is not present,
   wherein soot deposits present are detectable by measuring the conductivity between the electrodes and
   wherein the ceramic substrate is additionally provided with a layer which provides an high level of electrical insulation and which is simultaneously stable within exhaust gas.

12. A sensor for detecting soot, comprising:
   a ceramic substrate having an electrically nonconductive surface exposed to a measurement gas;
   an electrode structure formed on a the surface of the ceramic substrate and having electrodes for measuring electrical conductivity of the sensor;
   a heating system fitted to the substrate surface, said heating system setting a predefined operating temperature; and
   at least one temperature measuring device;
   wherein soot deposits present are detectable by measuring the conductivity between the electrodes, and
   wherein the heating system is simultaneously operable as a temperature sensor.

\* \* \* \* \*